United States Patent [19]
Fredberg

[11] 4,326,416
[45] Apr. 27, 1982

[54] ACOUSTIC PULSE RESPONSE MEASURING

[75] Inventor: Jeffrey J. Fredberg, Sharon, Mass.

[73] Assignee: Cambridge Collaborative, Inc., Cambridge, Mass.

[21] Appl. No.: 120,618

[22] Filed: Feb. 11, 1980

Related U.S. Application Data

[63] Continuation-in-part of Ser. No. 932,033, Aug. 8, 1978, abandoned.

[51] Int. Cl.$^3$ .............................................. G01N 24/00
[52] U.S. Cl. ........................................ 73/597; 128/720
[58] Field of Search ................... 128/720, 630; 73/574, 73/589, 597

[56] References Cited

U.S. PATENT DOCUMENTS

| | | | |
|---|---|---|---|
| 3,612,040 | 10/1971 | Sugiyama | 128/720 |
| 3,659,590 | 5/1972 | Jones et al. | 128/725 |
| 3,882,848 | 5/1975 | Klar et al. | 73/589 |
| 4,051,843 | 10/1977 | Franetzki et al. | 128/720 |
| 4,094,304 | 6/1978 | Wright, Jr. | 128/630 |
| 4,155,356 | 5/1979 | Venegos | 128/207.14 |

FOREIGN PATENT DOCUMENTS 206106  12/1967  U.S.S.R. .............................. 128/720

OTHER PUBLICATIONS

Jackson, A. C., et al., "Airway Geometry by Analysis of Acoustic Pulse Response Measurements", Jrnl. Appl. Phys., vol. 43, #3, pp. 523–536.
Fredberg, J. T., et al., "Canine Pulmonary Input Impedance Measured by Transient Forced Oscillations", Jrnl. Biomech. Engr., vol. 100, May 1978, pp. 67–71.
Ross, A., et al., "Direct Readout of Resp. Impedance", MBE, vol. 14, No. 5, Sep. 1976, pp. 558–564.
Dean, P.D., "An In-Situ Method of Wall Acoustic Impedance Measurement In Flow Ducts", Jrnl. Sound, Vib., vol 34, No. 1, May 8, 1974, pp. 99–130.
Goldman, M. et al., "A Simplified Measurement of Respiratory Resistance by Forced Oscillation", Jrnl. Appl. Phys., vol. 28, No. 1, Jan. 1970, pp. 113–116.
Landser, F. J. et al., "A New Method to Determine Frequency Characteristics of the Respiratory System", Jrnl. Appl. Phys., vol. 14, #1, Jul. 1976, pp. 101–106.
Table "(Composition of) Standard Atmosphere", p. 252, in *Scientific Tables*, published by Geigy–CIBA Ltd., Ardsley, NY 10502, © 1970.

*Primary Examiner*—Robert W. Michell
*Assistant Examiner*—Francis Jaworski
*Attorney, Agent, or Firm*—Charles Hieken

[57] ABSTRACT

A sound source located inside a tube having one end inside the mouth or nose of a subject provides an acoustic transient signal that propagates into the respiratory system of the subject to provide reflections sensed by a single mircophone inside the tube between the sound source and the mouth of the subject for recording on a transient recorder or computer and display on an oscilloscope after passing through a low pass filter to provide an output signal representative of the acoustical properties of the airways of the subject. This output signal may be processed in accordance with the deconvolution integral and other algorithms to determine essentially the acoustic impulse response, impedance or effective cross-sectional area of the airways, typically as a function of the distance from a reference point, such as the end of the tube.

14 Claims, 11 Drawing Figures

ACOUSTIC PULSE RESPONSE MEASURING

REFERENCE TO PRIOR COPENDING APPLICATION

This application is a continuation-in-part of copending Application Ser. No. 932,033 filed Aug. 8, 1978 now abandoned.

BACKGROUND OF THE INVENTION

The present invention relates in general to acoustic pulse response measuring and more particularly concerns novel apparatus and techniques for noninvasively obtaining a signal representative of the airways of a subject or of the acoustic reflection properties of a conduit or cavity. The invention is believed to be especially useful in evaluating the condition of human airways, for noninvasively determining the normal geometry, and the location of obstructions or leaks in a conduit, such as a sewer, water or gas pipe, and for providing a signal representative of the geometry of voice-producing regions for different phonemes helpful in teaching the deaf to speak.

For background information reference is made to an article entitled "Airway geometry by analysis of acoustic pulse response measurements" in the Journal of Applied Physiology for September 1977 beginning at page 523 listing Andrew C. Jackson et al. as authors and identifying the prior work of applicant. Reference is also made to an article entitled "Mechanical Response of the Lungs at High Frequencies" in Journal of Biomechanical Engineering for May 1978 beginning at page 57 by applicant and another and the following article entitled "Canine Pulmonary Input Impedance Measured by Transient Forced Oscillations" by applicant and others. Reference is also made to a paper by applicant el al. entitled "Airway Area by Acoustic Reflections Measured at the Mouth" published on pages 749-58 of JOURNAL OF APPLIED PHYSIOLOGY: RESPIRATORY, ENVIRONMENTAL AND EXERCISE PHYSIOLOGY (1980), portions of which are reproduced herein.

A typical prior art approach mentioned in the first cited article involves a steady-state measurement of the driving point acoustic impedance essentially at the airway opening of a subject excited by a pressure wave in the low bass frequencies determined by measuring the ratio of pressure to velocity at the opening at the excitation frequency. That article also makes reference to measuring impedance in this manner at still higher frequencies. While these measurements are interesting, it is difficult to associate the measurement results with meaningful physical conditions, such as abnormal constriction in the lungs. Furthermore, making the measurements is time-consuming for the subject, difficult and time-consuming for the experimenter, requires at least two pressure transducers needing tedious calibration and averages the results over many breaths, rather than providing information about the instantaneous configuration.

Accordingly, it is an important object of this invention to provide methods and means for providing a signal representative of the physical characteristics of conduits or cavities.

It is a further object of the invention to achieve the preceding object noninvasively.

It is still another object of the invention to achieve one or more of the preceding objects while overcoming one or more of the disadvantages noted above.

It is still a further object of the invention to provide an output signal containing characteristics that may be relatively easily evaluated to determine meaningful physical characteristics of the conduit or cavity.

It is a further object of the invention to achieve one or more of the preceding objects with respiratory measurements.

It is still another object of the invention to achieve one or more of the preceding objects with conduit measurements to provide meaningful information on leaks and/or obstructions.

It is still a further object of the invention to achieve one or more of the preceding objects with relatively low energy short duration acoustic pulses that do not damage the subject being examined according to the invention.

It is still a further object of the invention to achieve one or more of the preceding objects with a technique that provides a signal in form suitable for processing to provide acoustic impedance, or cross-sectional area, as a function of a distance that is especially useful in locating changes produced by abnormal openings or obstruction helpful in diagnosing the existence of the abnormal conditions.

It is still a further object of the invention to achieve one or more of the preceding objects with apparatus that is relatively inexpensive, reliable, rapid, easy to operate by relatively unskilled personnel and is relatively compact.

SUMMARY OF THE INVENTION

According to the invention, there is apparatus for providing a signal representative of the characteristics of a surrounded volume having an inlet including a conduit coupled to the inlet, and means for propagating an acoustic pulse through the conduit to the inlet to produce an acoustic echo signal representative of the physical properties of the surrounded volume. The conduit also includes electroacoustical transducing means preferably located between the source of the acoustic pulse and the inlet for providing an electrical signal representative of the echo signal, and means for processing the transduced electrical signal. The transduced signal may be applied to a transient recorder or computer, and/or applied to a low-pass filter typically having a cutoff at approximately 10 kHz in air, but at various frequencies depending upon gas contained in the cavity, and then displayed on an oscilloscope. Alternatively, the resultant signal may be processed in accordance with the deconvolution integral to determine the impulse response of the frequency and phase response as a function of frequency of the surrounded volume.

The method according to the invention includes connecting the end of the conduit to the inlet, propagating an acoustic pulse through the conduit into the surrounded volume, and detecting the echo signal reflected from the surrounded volume back through the inlet into the conduit.

Numerous other features, objects and advantages of the invention will become apparent from the following specification when read in connection with the accompanying drawing in which:

DETAILED DESCRIPTION OF PREFERRED EMBODIMENTS

Figure 1:
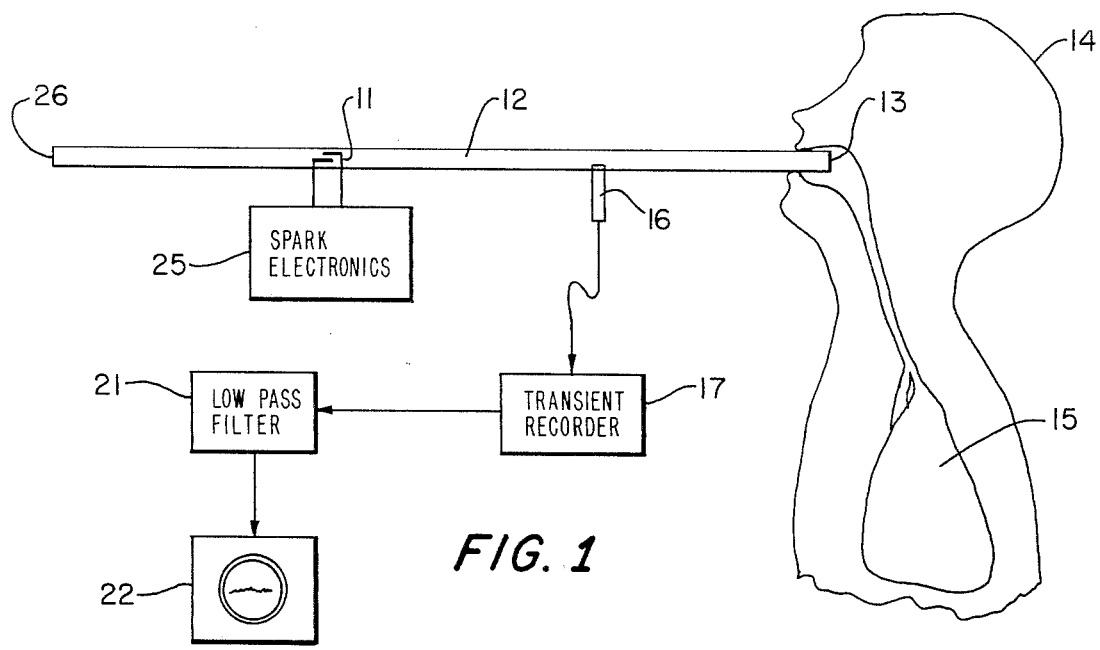
FIG. 1 is a combined block-pictorial diagram illustrating the logical arrangement of a system according to the invention.

With reference now to the drawing and more particularly FIG. 1 thereof, there is shown a combined block-pictorial diagram illustrating the logical arrangement of a system according to the invention. A sound source 11, which may comprise a spark gap or other suitable source of a sound pulse, in a tube 12 having one end 13 inside the throat of subject 14 emits a pressure wave transient that enters the inlet of lungs 15 to produce a reflected wave that returns through opening 13 and propagates back to sound source 11 to impinge upon microphone 16 that produces a corresponding electrical signal delivered to transient recorder 17. The output of transient recorder 17 is delivered to low-pass filter 21 having a cutoff frequency typically of 6 to 12 kHz for application to oscilloscope 22 to provide a signal waveform such as that shown in FIG. 2 representative of the characteristics of the lungs of subject 15.

Figure 2:
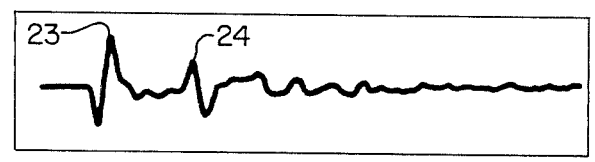
FIG. 2 is a graphical representation of a detected filtered signal produced by an acoustic pulse propagated into the lungs of a human.

FIG. 2 is a graphical representation of the waveform provided by microphone 16 as a function of time. The first pulse 23 is the incident pulse provided by sound source 11 as it passes microphone 16. The second oppositely phased pulse of smaller amplitude 24 is the reflection from the incident pulse at the boundary between opening 13 and the inlet to the lungs 15, the remaining portions being reflections from the lungs and characteristic of the physical properties of them. Since the waveform is presented as a function of time and the velocity of propagation of sound known within a reasonable tolerance, the various portions of the signal waveform may be associated with distances from opening 13 so that particular signal peaks and valleys may be associated within a reasonable degree of accuracy to particular locations of the airways. When the invention is used for examining pipes or other conduits or cavities for obstructions or openings, particular irregularities in the reflected waveform may be interpreted as a leak or obstruction at a particular distance along the conduit or cavity length to facilitate promptly finding the leak or obstruction and correcting it.

Spark source 11 is energized by associated spark electronics 25 of known form. Tube 12 may be one 2" plexiglass tube preferably having end 26 further from microphone 16 than the end of lungs 15 so that the initial reflection from opening 26 occurs after the reflection from the point in lungs 15 furthest from microphone 16.

Microphone 16 may be a B&K ⅛" diameter microphone, transient recorder 17 may be a commercially available Biomation transient recorder and low-pass filter 21 may be a commercially available Ithaco filter.

Figure 3:
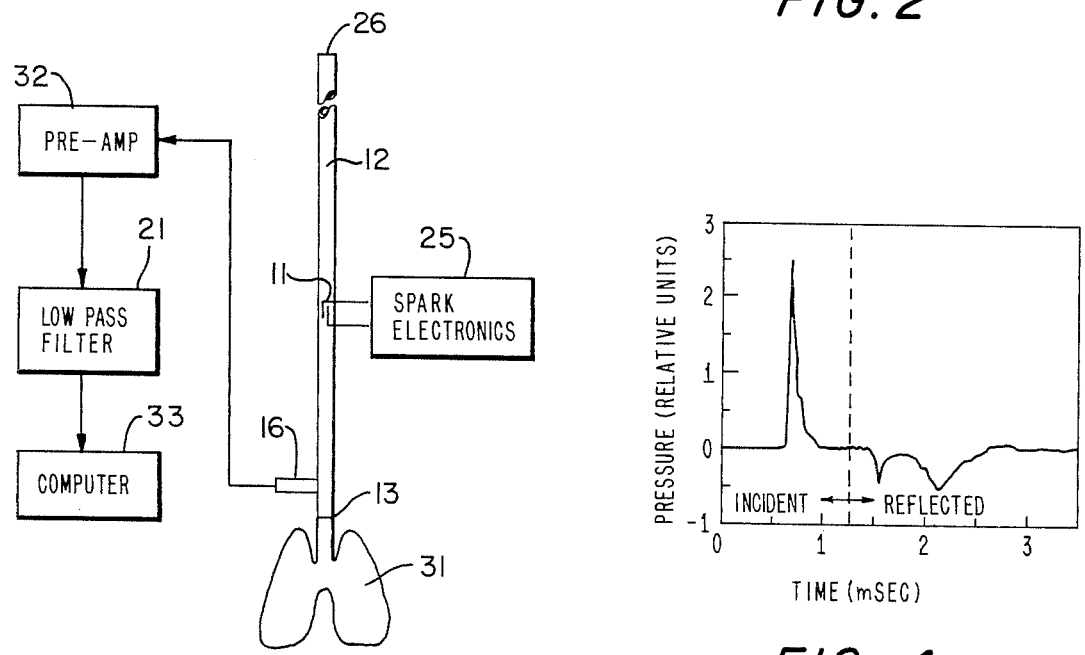
FIG. 3 is a combined block-pictorial diagram illustrating the logical arrangement of a system according to the invention for measuring the properties of an excised lung.

Referring to FIG. 3, there is shown a combined block-pictorial diagram of another embodiment of the invention shown arranged for measuring the characteristics of an excised lung 31. The same reference numerals identify corresponding elements throughout the drawing. Sound source 11 propagates a pressure wave transient that enters excised lung 31 through opening 13 to produce a reflected wave that returns to tube 12 through opening 13 and is detected by microphone 16 to provide a corresponding electrical signal amplified by preamplifier 32 and delivered through low-pass filter 21 to computer 33 that may then process the signal in accordance with known techniques to produce the normalized impedance and phase as a function of frequency shown in FIG. 5 for a typical freshly excised dog lung inflated by positive transpulmonary pressure of 35 cm $H_2O$ reduced to 25 cm, then reinflated to 35 cm and reduced to a specified transpulmonary pressure that was maintained for 5 minutes prior to collecting data. The particular techniques for performing the deconvolution integral with a digital computer on a number of sample microphone responses to a spark transient are not a part of the invention, known in the art and not described herein to avoid obscuring the principles of the invention.

Figure 4:
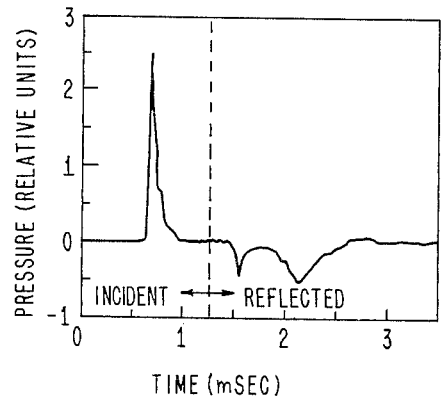
FIG. 4 shows the pressure as a function of time at the microphone representative of the incident spark-generated pressure pulse and the waves reflected from the lung inlet.

Referring to FIG. 4, there is shown the pressure history at microphone 16 showing the incident spark-generated pressure pulse followed by the waves reflected from opening 13.

Figure 5:
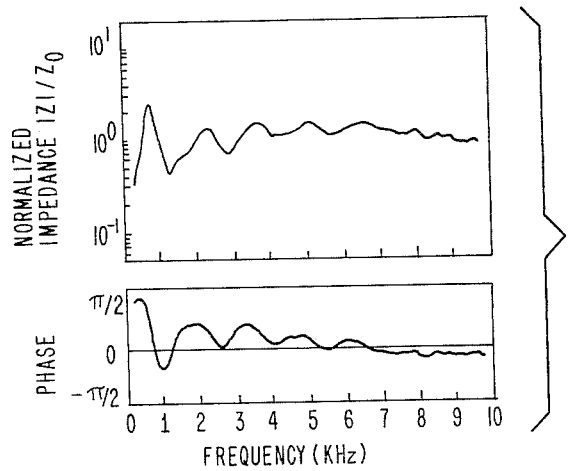
FIG. 5 is a graphical representation of normalized impedance and phase as a function of frequency of an animal lung.

The input impedance such as that shown in FIG. 5 may be converted to the complex reflection coefficient as a function of frequency of a rigid-walled transmission line possessing the same cross-sectional area as the trachea ($A_o$) and terminated by the lung coupled to opening 13:

$$R(f_n) = \frac{Z_{in}(f_n) - \frac{\rho c}{A_0}}{Z_{in}(f_n) + \frac{\rho c}{A_0}}$$

Figure 6:
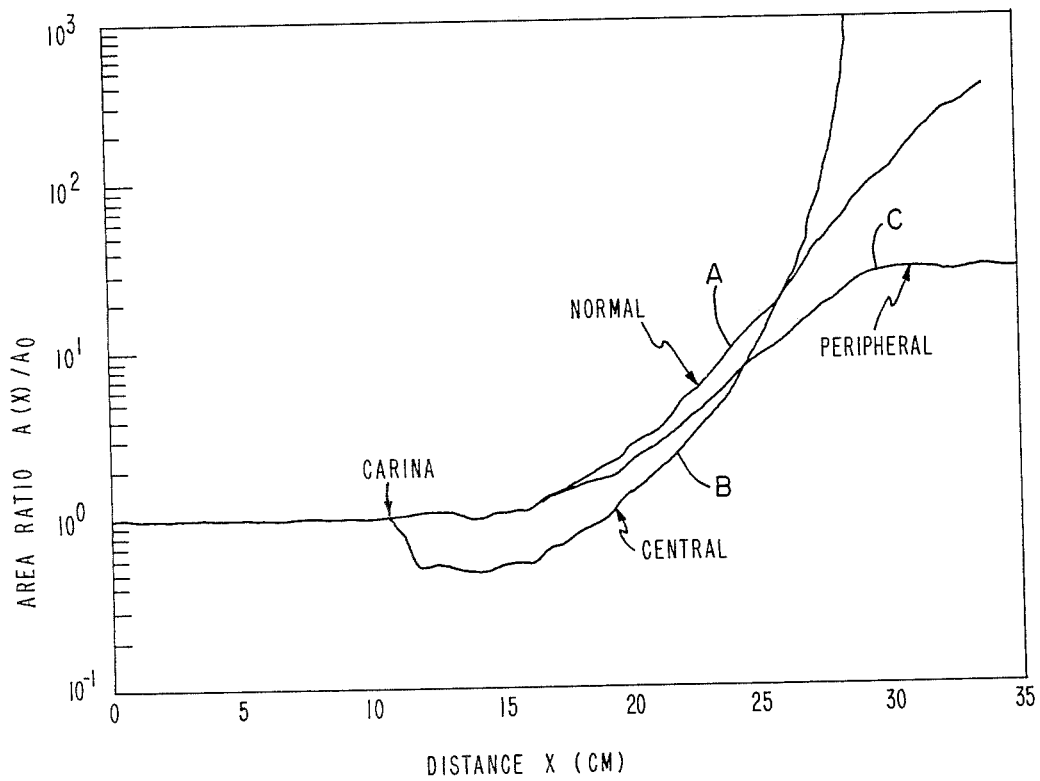
FIG. 6 is a graphical representation of cross sectional area as a function of distance from an opening normalized with respect to the cross sectional area at the inlet for normal, centrally constricted and peripherally constricted rigid-walled structures determined by using reflection coefficient techniques.

The reflection coefficient is the Fourier transform of the impulse response $h(t_n)$ for discrete time $t_n$, $\rho$ is the density of the medium and c is the velocity of sound in the medium. Computing $h(t_n)$ produces a sequence that may be processed by the Ware-Aki algorithm to produce the area-travel time (or distance) inversion. If distance is defined as the distance traveled in time t at free gas speed $c_0$, then an area-distance inference can be computed and is typically shown in FIG. 6. FIG. 6 shows area ratio as a function of distance with the carina being at substantially 10 cm. The walls are assumed to be nonrigid and curve B with central constrictions in the region between 10 and 25 centimeters has a smaller area ratio than normal curve A while beginning at about 17 cm curve C indicates peripheral restrictions with an area ratio less than that of normal curve A. The Ware-Aki algorithm is described in their article entitled "Continuous and Discrete Inverse-Scattering Problems in a Stratified Elastic Medium. I. Plane Waves at Normal Incidence," J. Acoust. Soc. Am., 54, 4, 911-921, (1969).

The invention is especially useful for providing a signal representative of the geometry of voice-producing regions for different phonemes helpful in teaching the deaf to speak. To this end it is convenient to provide a graphical display of the type shown in FIG. 6 representative of the area as a function of distance from the mouth so that variations in tongue position for the different phonemes are readily observable by a deaf person and the teacher. Preferably the signals are processed substantially in real time so that the display essentially tracks the tongue position as phonemes are uttered. To this end the opening 13 is placed substantially at the lips and may be typically coupled to the mouth through a flexible seal, preferably covering the lips while allowing movement of them as phonemes are uttered.

Figure 7:
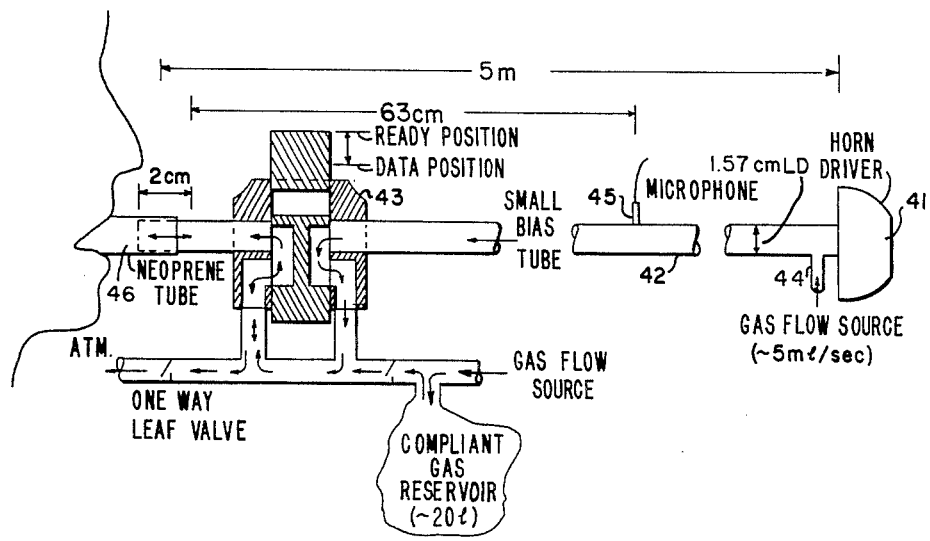
FIG. 7 is a diagrammatic representation of experimental apparatus according to the invention.

Referring to FIG. 7, there is shown a diagrammatic representation of actual experimental apparatus according to the invention. The apparatus comprises a loudspeaker 41 (University I.D.—60 horn driver, 12 kHz bandwidth), a 5 meter stainless steel tube 42 of constant 1.57 cm internal diameter, and a sliding two-position valve 43. With the valve in the ready position as shown the subject breathed either room air or a humidified mixture of He (80%) and $O_2$ (20%). With the valve in the data acquisition position the subject was placed in line with the wave tube 42. A small bias flow of gas through inlet 44 from the loudspeaker towards the subject maintained uniform gas composition.

A 16 bit minicomputer (Data General NOVA 2) (not shown) emitted a transient signal through a digital-to-analogue converter (not shown) into an amplifier (not shown) (Crown DT-60) powering the horn driver 41, which in turn launched the incident transient towards the subject. The shape of the transient signal stored in the computer was (in 50 μs steps) 0, 1, 1, 1, 1, 0, 0, 0, 1, 1, 1, 0 volts. The incident transient and its reflection from the subject were transduced by a 1/10" diameter piezoelectric microphone 45 (Bolt, Beranek, and Newman, model 377) mounted flush with the wave tube wall 65 cm from the subject. The microphone output was fed to a preamplifier (not shown), a 4-pole 12 kHz low-pass filter (not shown), another preamplifier (not shown), and an analogue-to-digital converter (not shown) sampling at a rate of 33 kHz. The digitized data were processed by the same NOVA 2 minicomputer.

A special calibration procedure separated the incident transient from its reflection. A rubber stopper attached to a rod was lodged in the tube near the microphone. With the stopper in place the microphone output transient, Pcal(t), was proportional to the incident wave pressure Pi(t) as shown in the upper trace in FIG. 8. If the stopper were perfectly reflecting, then the constant of proportionality, $\alpha$, would be equal to 2 and the waveform Pcal(t) would become the incident wave superposed upon an identical image reflection. Pcal(t) was recorded for approximately 22 ms in air, and 11 ms in the $He-O_2$ mixture at which time secondary reflections from the loudspeaker 41 arrived at the microphone.

Figure 8:
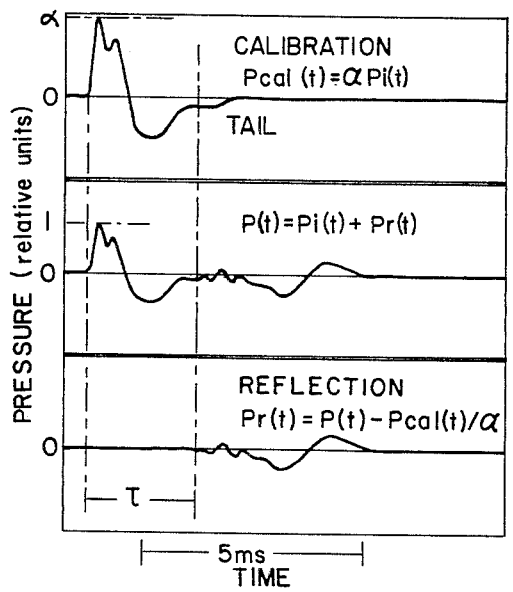
FIG. 8 is a graphical representation of pressure amplitude as a function of time at the microphone during calibration, data acquisition and extracted reflected wave.

With the stopper removed and the subject in place, the microphone output, P(t), consisted of the incident wave Pi(t) superposed upon the delayed reflection from the subject Pr(t) as shown in the middle trace in FIG. 8. The round trip propagation delay, from microphone to subject to microphone, was $\tau$. The reflected wave shown in trace of FIG. 8 was extracted by the subtraction Pr(t) = P(t) − Pcal(t)/$\alpha$, and $\alpha$ was determined by minimizing the mean square differences between the calibration signal, Pcal(t), and the data signal P(t), for all time less than $\tau$. This calibration was repeated before each experiment to eliminate the effects of slow changes in room temperature and variations in gas composition observed with prolonged use of the compressed $He-O_2$ tank.

The time windows for the incident and reflected waves were weighted by unity over the first 15/16 of the data window and were smoothly tapered to zero at the end using one-half cycle of a cosine function over the last 1/16 of the window. The incident and reflected data windows lasted 10 and 22 ms, respectively, using air, and 5 and 11 ms using $He-O_2$.

Figure 9:
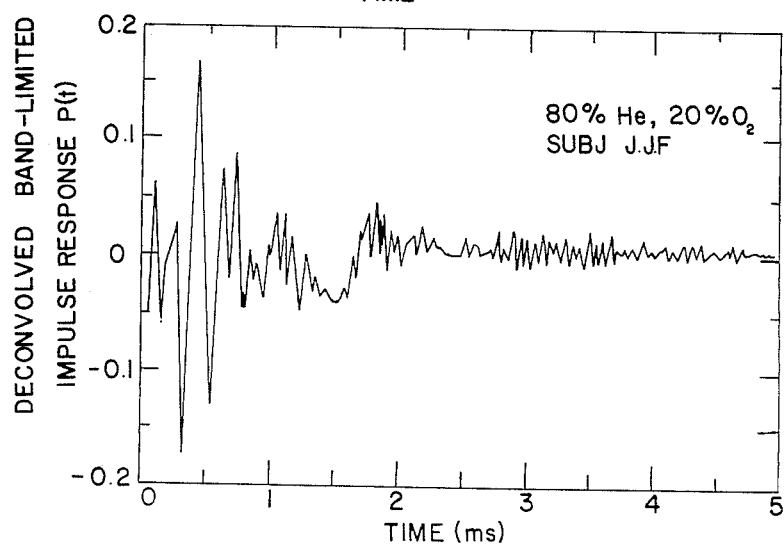
FIG. 9 shows the deconvolved band-limited impulse response representing echoes and reverberations of incident waves from impedance inhomogeneities along the airway.

Incident and reflected data were deconvolved by standard frequency domain techniques to obtain the impulse response of the subject shown in FIG. 9. In the case of air the Fourier transforms of the incident and reflected waves were computed and divided. A second calibration procedure removed the attenuation and transmission delay of 63 cm of wave tube 42 separating the subject from the microphone 45 as described in reference 5 of the aforesaid 1980 paper of applicant et al. The result was numerically filtered by a uniform-phase four-pole low-pass filter at 6 kHz. The inverse Fourier transform was then computed yielding the band-limited impulse response. D.C. biases which arose in the impulse response from computational error, noise, and windowing were suppressed by subtraction of the real part of the impulse response averaged over all negative time, thus satisfying the condition of causality.

In the case of the $He-O_2$ mixture the enhanced bandwidth (12 kHz) necessitated noise suppression measures. Rather than simple inverse transformation, the band-limited impulse response shown in FIG. 9 was computed by applying the Hunt deconvolution method described in reference 6 in said 1980 paper, preceded by a uniform phase 4-pole low-pass filter at 12 kHz. D.C. biases were suppressed. The impulse response was mapped into an area inference by the Ware-Aki algorithm in reference 14 of said 1980 paper as described by Sidell and Fredberg in reference 11 of said 1980 paper.

Figure 10:
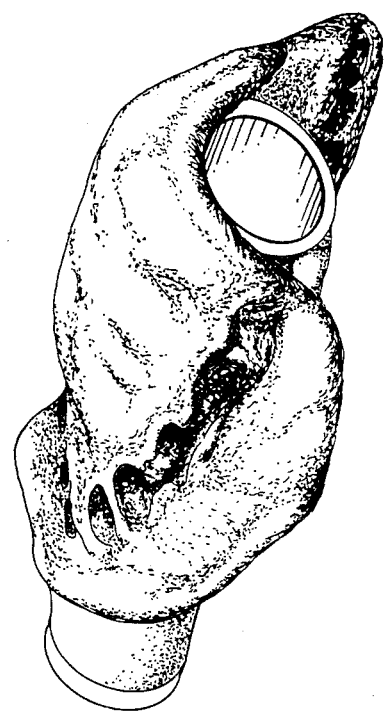
FIG. 10 is a perspective view of a casted mouthpiece that fills all oral interstices between posterior margin of hard palate and lips.
Figure 11:
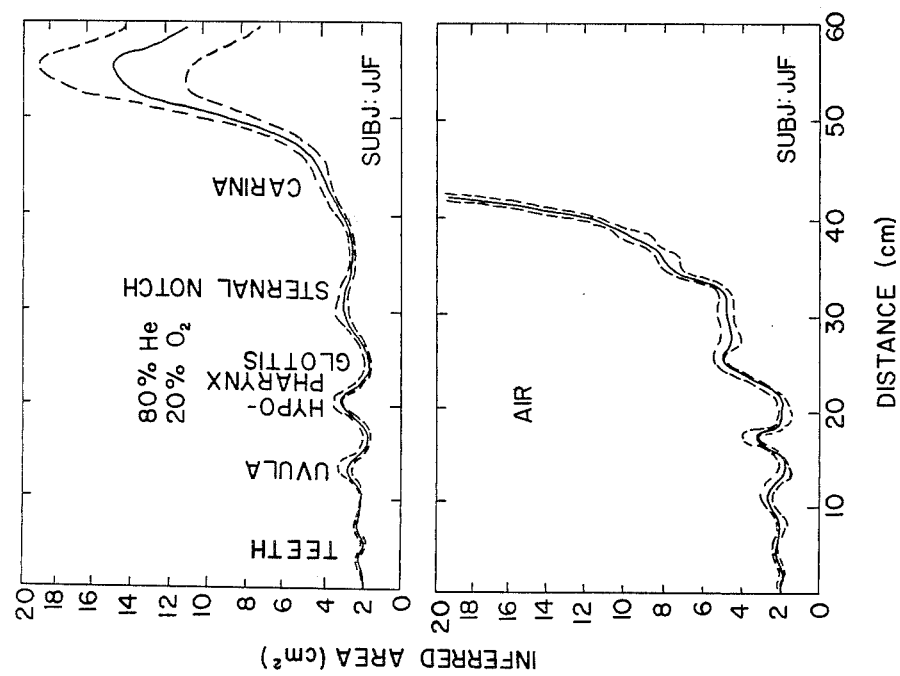
FIG. 11 is a graphical representation of the inferred airway area as a function of distance along the airway illustrating the significant differences between using a mixture of predominantly helium and oxygen relative to using air alone, with familiar anatomic landmarks along the airway identified from radiographs based on measurements made of applicant.

The area inference theory assumes one-dimensional wavefronts at all points in the airway. This is approximately true for frequencies f satisfying the relation $$f < c_o/(2d_{max})$$

where $d_{max}$ is the largest transverse dimension way of the air and $c_o$ is the gas wavespeed as explained in reference 10 of said 1980 paper. Using the mouthpiece described below and shown in FIG. 10 $d_{max}$ is 2–3 cm, allowing 6 kHz analysis bandwidth when subjects breathe air, and 12 kHz analysis bandwidth when subjects breathe 80% He, 20% $O_2$.

It has been observed that the spatial resolution of the area inference is approximately equal to one-sixth of the gas wavespeed divided by the analysis bandwidth. See said reference 11, Appendix. Recalling that the maximum analysis bandwidth is $c_o/2d_{max}$, it follows that the resolution of the area inference can be no smaller than $d_{max}/3$, as a rough approximation. In the human airways the largest transverse dimension is often in the mouth from cheek to cheek (4–8 cm). In an effort to achieve finer spatial resolution and greater bandwidth within this constraint, and to limit variability associated with tongue and jaw position, and cheek compliance, a casted mouthpiece shown in FIG. 10 of the oral cavity is used penetrated by a relatively straight and uniform neoprene rubber tube 46 (2 cm internal diameter and 1.6 mm wall thickness). This case was made from a non-toxic dental casting material (Neoplex, Lactona Co., New Jersey). Before the material was set it was molded by hand around the neoprene rubber rube 46 in the approximate shape of the subject's oral cavity. During molding the rubber tube 46 was buttressed internally by a 1 cm diameter rod to prevent collapse. The subject was instructed to insert the casting material into his mouth and then to bite while lifting and pressing the cast with his tongue. Excess material was extruded into the cheek pouches. This procedure yielded a comfortable, well-fit, reusable mouthpiece with a definable decrease in area where the front teeth bit the tube shown in FIG. 10.

It is necessary that the naso-pharyngeal aperture (velum) be closed during data acquisition so that the airway can be modelled as a one-dimensional duct of varying area. It was found that the velum remained closed during mouth breathing only if nose clips were not used.

Six healthy adults were studied during the normal tidal breathing following an inspiration to total lung capacity. During early inspiration the valve was thrown from the ready to the data acquisition position, interrupting inspiration. Within ½ second the transient response was acquired, the valve was returned to the ready position, and inspiration resumed. In most trials the glottis remained open during this procedure and airway pressure was slightly negative.

In each subject data were acquired on 5 separate breaths with air and with He-$O_2$. Each transient response was stored and processed individually to yield an area inference. For each sequence of 5 the mean and standard deviation of the area inferences were computed. In two instances the data were extremely variable probably because of glottal closure; these two subjects were restudied with good results.

There has been described novel apparatus and techniques for noninvasively determining physical characteristics of conduits and cavities, such as human airways and pipes without damage. It is evident that those skilled in the art may now make numerous uses and modifications of and departures from the specific apparatus and techniques herein disclosed without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. Apparatus for measuring physical properties of a confined volume comprising, conduit means for exchanging acoustical energy with said confined volume, means for propagating a pressure pulse within said conduit through an opening thereof for entry into the confined volume, electroacoustical transducing means in said conduit responsive to acoustical energy therein for providing an electrical signal representative of wave energy having spectral components in a substantial portion of the audio frequency range above 100 Hz reflected through said opening in response to said pressure pulse propagated through said opening provided by said means for propagating, and utilization means responsive to said detected signal for providing a representation thereof characteristic of physical properties of said confined volume, said physical properties including the cross sectional area of said confined volume as a function of its distance from said opening.

2. Apparatus in accordance with claim 1 wherein said means for propagating comprises a sound source inside said conduit means.

3. Apparatus in accordance with claim 1 and further comprising said confined volume connected to said opening.

4. Apparatus in accordance with claim 1 wherein said conduit means has a second opening with the distance between said second opening and said electroacoustic transducing means being greater than the distance between said electroacoustic transducing means and the furthest point of interest in said confined volume, whereby reflected wave energy from said confined volume enters said first-mentioned opening and arrives at said electroacoustic transducing means before wave energy reflected from the second-mentioned opening.

5. Apparatus for measuring physical properties of a confined volume in accordance with claim 1 wherein said electroacoustical transducing means comprises a single microphone.

6. Apparatus for measuring physical properties of a confined volume in accordance with claim 1 and further comprising, means for injecting into said confined volume prior to propagating said pressure pulse a mixture of a gas having a density less than that of air with oxygen.

7. Apparatus for measuring physical properties in accordance with claim 6 wherein said gas is helium.

8. Apparatus for measuring physical properties of a confined volume in accordance with claim 7 wherein said mixture is substantially 80% helium and 20% oxygen.

9. A method of measuring physical properties of a confined volume which method includes the steps of, connecting the opening of a conduit to an entrance to said confined volume, propagating a pressure pulse inside said conduit through said opening, and detecting wave energy having spectral components in a substantial portion of the audio frequency range above 100 Hz reflected through said opening as it arrives at electroacoustical transducing means in said conduit to provide an electrical signal representative of physical characteristics of said confined volume connected to said opening, said physical characteristics including the cross sectional area of said confined volume as a function of the cross sectional area distance from said opening.

10. A method in accordance with claim 9 wherein said entrance is the mouth of a subject and further including the steps of processing said electrical signal to provide a visual representation of airway cross sectional area as a function of distance from the mouth.

11. A method in accordance with claim 10 and further including the step of uttering phonemes and observing said visual display.

12. A method in accordance with claim 10 and further including the step of injecting a mixture of a gas having a density less than that of air with oxygen through said mouth before propagating said pressure pulse.

13. A method in accordance with claim 12 wherein said gas is helium.

14. A method in accordance with claim 13 wherein said mixture is substantially 80% helium and 20% oxygen.

* * * * *

REEXAMINATION CERTIFICATE (2019th)

United States Patent [19]

Fredberg

[11] B1 4,326,416

[45] Certificate Issued May 25, 1993

[54] ACOUSTIC PULSE RESPONSE MEASURING

[75] Inventor: Jeffrey J. Fredberg, 27 Tall Tree Rd., Sharon, Mass. 02067

[73] Assignee: Jeffrey J. Fredberg, Sharon, Mass.

Reexamination Request:
No. 90/002,400, Aug. 14, 1991

Reexamination Certificate for:
Patent No.: 4,326,416
Issued: Apr. 27, 1982
Appl. No.: 120,618
Filed: Feb. 11, 1980

Related U.S. Application Data

[63] Continuation-in-part of Ser. No. 932,033, Aug. 8, 1978, abandoned.

[51] Int. Cl.$^5$ .......................... A61B 5/08; G01N 24/00
[52] U.S. Cl. ........................................ 128/720; 73/597
[58] Field of Search ................... 128/720, 630; 73/574, 73/589, 597

[56] References Cited

U.S. PATENT DOCUMENTS

| | | | |
|---|---|---|---|
| 3,612,040 | 10/1971 | Sugiyama | 128/720 |
| 3,659,590 | 5/1972 | Jones et al. | 128/725 |
| 3,882,848 | 5/1975 | Klar et al. | 73/589 |
| 4,051,843 | 10/1977 | Franetzki et al. | 128/720 |
| 4,094,304 | 6/1978 | Wright, Jr. | 128/630 |
| 4,155,356 | 5/1979 | Venegos | 128/204.23 |

OTHER PUBLICATIONS

M. R. Schroeder, "Determination of the Geometry of the Human Vocal Tract by Acoustic Measurements", J. Acous. Soc. Amer., vol. 41, #4, Part 2, 1967, pp. 1002-1010.
Sondhi, M. M. et al, "Determination of Vocal-Tract Shape from Impulse Response at the Lips", J. Acoust. Soc. of America, vol. 49, No. 6, Part 2, 1971, pp. 1867-1873.
Fredberg, J. J. et al, "Measurement of Acoustic Impedance of an Excised Canine Pulmonary System by Transient Excitation", Abstract 4:45, J. Acoustic Society America, vol. 58, Supp. No. 1, Fall 1975, p. S128.
*Physics News in 1978,* "Acoustics: Acoustical Properties of the Vocal Tract", Present, G. (editor), Amer. Inst. of Physics Publ. ©1978, pp. 1-3.
Sondhi, M. et al, "The Inverse Problem for the Vocal Tract: Numerical Methods, Acoustic Experiments, and Speech Synthesis", Jrnl. Ac. Society of Amer. 73(3) Mar. 1983 (pp. 985-1002).
Sondhi, M. "Estimation of Vocal-Tract Areas: The Need for Acoustical Measurements", IEEE Trans. on Acoustics, Speech & Sig. Processing, vol. ASSP-27 #3, Jun. 1979.
Jackson, A. C. et al. "Airway Geometry by Analysis of Acoustic Pulse Response Measurements", Jrnl. Appl. Physics, vol. 43 #3, pp. 523-536.
Fredberg, J. J. et al. "Canine Pulmonary Input Impedance Measured by Transient Forced Oscillations", Jrnl. Biomech. Engr. vol. 100, May 1978, pp. 67-71.
Ross, A. et al. "Direct Readout of Respiratory Impedance", MBE vol. 14, No. 5, Sep. 1976, pp. 558-564.
Dean, P. D. "An In-Situ Method of Wall Acoustic Impedance Measurement In Flow Ducts", Jrnl. Sound Vibrations, vol. 34 No. 1, May 8, 1974, pp. 99-130.
Goldman, M. et al. "A Simplified Measurement of Resp. Resistance by Forced Oscillation", Jrnl. Appl. Physics vol. 28 No. 1, Jan. 1970, pp. 113-116.
Landser, F. J. et al, "A New Method to Determine Freq. Characteristics of the Respiratory System", Jrnl. Appl. Physics vol. 14 #1, Jul. 1976, pp. 101-106.
Table "(Composition of) Standard Atmosphere", p. 252 in *Scientific Tables,* published by Geigy-CIBA Ltd., Ardsley, N.Y. 10502, ©1970.

*Primary Examiner*—Francis Jaworski

[57] ABSTRACT

A sound source located inside a tube having one end inside the mouth or nose of a subject provides an acoustic transient signal that propagates into the respiratory system of the subject to provide reflections sensed by a single microphone inside the tube between the sound source and the mouth of the subject for recording on a transient recorder or computer and display on an oscil-

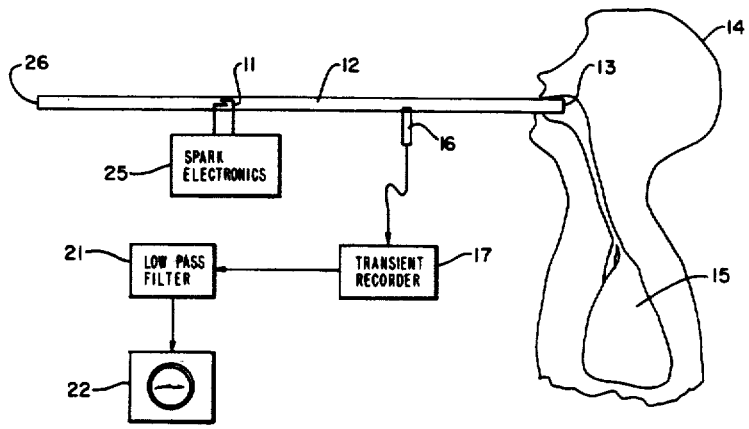

loscope after passing through a low pass filter to provide an output signal representative of the acoustical properties of the airways of the subject. This output signal may be processed in accordance with the deconvolution integral and other algorithms to determine essentially the acoustic impulse response, impedance or effective cross-sectional area of the airways, typically as a function of the distance from a reference point, such as the end of the tube.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, lines 37-57:
According to the invention, there is apparatus for providing a signal representative of the characteristics of a surrounded volume *or confined volume passageway* having an inlet *or entrance in a living subject* including a conduit coupled to the inlet, and means for propagating an acoustic *pressure* pulse through the conduit *and a piece at one end* to the inlet to produce *substantially one-dimensional wavefronts in response to the pressure pulse at substantially all points in the passageway and* an acoustic echo signal representative of the physical properties of the surrounded volume. The conduit also includes electroacoustical transducing means preferably located between the source of the acoustic pulse and the inlet for providing an electrical signal representative of the echo signal, and means for processing the transduced electrical signal. The transduced signal may be applied to a transient recorder or computer, and/or applied to a low-pass filter typically having a cutoff at approximately 10 kHz in air, but at various frequencies depending upon gas contained in the cavity, and then displayed on an oscilloscope. Alternatively, the resultant signal may be processed in accordance with the deconvolution integral to determine the impulse response of the frequency and phase response as a function of frequency of the surrounded volume.

AS A RESULT OF REEXAMINATION, IT HAS BEEN DETERMINED THAT:

Claims 1, 3-4, 6 and 9 are determined to be patentable as amended.

Claims 2, 5, 7-8 and 10-14, dependent on an amended claim, are determined to be patentable.

New claims 15-19 are added and determined to be patentable.

1. Apparatus for measuring physical properties of a confined volume *passageway having an entrance in a living subject* comprising,
conduit means for exchanging acoustical energy with said confined volume *passageway*,
*a piece at one end of said conduit means for engaging said entrance*,
means for propagating a pressure pulse within said conduit *means* through an opening thereof *and said piece* for entry into the confined volume *passageway*,
*said piece and conduit means constructed and arranged to produce substantially one-dimensional wavefronts in response to said pressure pulse at substantially all points in said confined volume passageway when said piece engages said entrance*,
electroacoustical transducing means in said conduit responsive to acoustical energy therein for providing an electrical signal representative of wave energy having spectral components in a substantial portion of the audio frequency range above 100 Hz reflected through said opening in response to said pressure pulse propagated through said opening provided by said means for propagating,
and utilization means responsive to said [detected] *electrical* signal for providing a representation thereof characteristic of physical properties of said confined volume *passageway*,
said physical properties including the cross sectional area of said confined volume *passageway* as a function of its distance from said opening.

3. Apparatus in accordance with claim 1 and further comprising said confined volume *passageway entrance engaging said piece and adapted to be* connected to said opening.

4. Apparatus in accordance with claim 1 wherein said conduit means has a second opening with the distance between said second opening and said electroacoustic transducing means being greater than the distance between said electroacoustic transducing means and the furthest point of interest in said confined volume *passageway*,
whereby reflected wave energy from said confined volume *passageway* enters said first-mentioned opening and arrives at said electroacoustic transducing means before wave energy reflected from the second-mentioned opening.

6. Apparatus for measuring physical properties of a confined volume [detected in accordance with claim 1] *comprising*,
*conduit means for exchanging acoustical energy with said confined volume*,
*means for propagating a pressure pulse within said conduit through an opening thereof for entry into the confined volume*,
*electroacoustical transducing means in said conduit responsive to acoustical energy therein for providing an electrical signal representative of wave energy having spectral components in a substantial portion of the audio frequency range above 100 Hz reflected through said opening in response to said pressure pulse propagated through said opening provided by said means for propagating*,
*and utilization means responsive to said electrical signal for providing a representation thereof characteristic of physical properties of said confined volume*,
*said physical properties including the cross sectional area of said confined volume as a function of its distance from said opening*,
and further comprising, means for injecting into said confined volume prior to propagating said pressure pulse a mixture of a gas having a density less than that of air with oxygen.

9. A method of measuring physical properties of a confined volume *passageway in a living subject* which method includes the steps of connecting the opening of a conduit to an entrance to said confined volume *passageway*,
propagating a pressure pulse inside said conduit through said opening *to produce substantially one-* dimensional wavefronts at substantially all points in said passageway and said conduit, and detecting wave energy having spectral components in a substantial portion of the audio frequency range above 100 Hz reflected through said opening as it arrives at electroacoustical transducing means in said conduit to provide an electrical signal representative of physical characteristics of said confined volume *passageway* connected to said opening, said physical characteristics including the cross sectional area of said confined volume *passageway* as a function of the cross sectional area distance from said opening.

15. Apparatus for measuring physical properties of a confined volume passageway in a living subject in accordance with claim 1 and further comprising, said piece being adapted to engage said living subject, through said opening being inside said living subject.

16. Apparatus for measuring physical properties of a confined volume passageway in a living subject in accordance with claim 15 and further comprising, said piece attached to said conduit adapted to be connected at said opening.

17. Apparatus for measuring physical properties of a confined volume passageway in a living subject in accordance with claim 16 wherein said living subject has an oral cavity and said piece is a mouthpiece adapted to be seated inside said oral cavity.

18. Apparatus for measuring physical properties of a confined volume passageway in a living subject in accordance with claim 17 wherein said mouthpiece has substantially the shape of said oral cavity.

19. Apparatus in accordance with claim 1 wherein the ratio of twice the largest transverse dimension of said confined volume passageway to the gas wave speed in said confined volume passageway is greater than the inverse of the frequency of spectral components of said electrical signal providing said representation thereof characteristic of said physical properties of said confined volume passageway.

* * * * *